US00PP29217P2

(12) United States Plant Patent
Stapleton et al.

(10) Patent No.: US PP29,217 P2
(45) Date of Patent: Apr. 10, 2018

(54) COAST REDWOOD TREE WITH PERICLINAL CHIMERIC ALBINISM NAMED 'EARLY SNOW'

(50) Latin Name: *Sequoia sempervirens*
Varietal Denomination: Early Snow

(71) Applicant: Thomas Santos Stapleton, Volcano, CA (US)

(72) Inventors: Thomas Santos Stapleton, Volcano, CA (US); Dale Frederick Holderman, Santa Cruz, CA (US)

(73) Assignee: Thomas Santos Stapleton, Volcano, CA (US)

( * ) Notice: Subject to any disclaimer, the term of this patent is extended or adjusted under 35 U.S.C. 154(b) by 0 days.

(21) Appl. No.: 15/530,139

(22) Filed: Dec. 6, 2016

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Annette H Para

(57) ABSTRACT

'Early Snow' is a new and distinct variety of albino coast redwood tree characterized by a non-grafted, periclinal chimera exhibiting stable albino growth from inside the apical meristem dome and with terminal buds exhibiting phenotypic color expressions of green, albino, chimera or non-chimeric variegation with varying hues within these color expressions. The new variety also has dark green short to medium length needles, branches exhibiting horizontal to drooping-like habit and with the shape of branchlets tapering towards a blunt end, and moderate-to-fast growth depending on the amount of albinism. Further, the latent, axillary and/or accessory buds forming between the internode of primary branches, branch axils, leaf axils, and within the branch collar zone, express a higher amount of albinism within the internode. Frequently, axillary and/or accessory buds form in the absence of an existing branch, whether it's primary or secondary in nature.

9 Drawing Sheets

Figure 1:
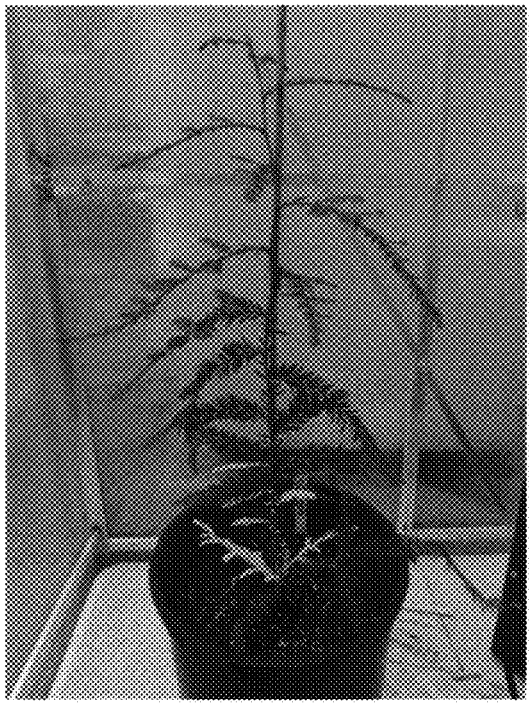

Latin name of the genus and species of the tree claimed: The Coast Redwood tree variety of this invention is botanically identified as *Sequoia sempervirens*.

Variety denomination: The variety denomination is 'Early Snow'.

BACKGROUND OF THE INVENTION

The present invention relates to a new and distinct tree variety of *Sequoia sempervirens*, more commonly known as Coast Redwood tree, having naturally-occurring chimeric characteristics resulting in albinism vegetation.

Specifically, 'Early Snow' is a periclinal chimera exhibiting stable albino growth inside the apical meristem dome. The albinism emerges more prominently beginning in the first or second year of growth. Tests conducted by the first-named inventor reveal that the present invention has a survival tolerance with up to 65 to 70 percent albinism. The buds of the present invention contain several forms of naturally-occurring chimera, including: periclinal, mericlinal, and sectorial. The branches demonstrate color variation, including: green, albino, and chimeric, and non-chimeric variegation; and exhibit a horizontal-to-moderate drooping growth habit. Needle morpholgy exibits a dense, occasionally overlaping habit that is singularly arranged with a concave pattern. Additionally, certain favorable conditions, the present invention yields high propagation levels via stem and leaf cuttings.

The new variety originated as a result of an ongoing breeding program in Santa Cruz, Calif. The seedling of the present invention was grown from a controlled cross conducted in 1976 where an unnamed, unpatented albino

*Sequoia sempervirens* providing the male pollen and the conelets of an unnamed, unpatented green *Sequoia sempervirens* were pollinated. After repeated experimental propagation efforts, asexually-reproduced leaf and stem cuttings took root in a greenhouse laboratory setting in Volcano, Calif. between the years of 2012-2015. These cuttings yielded the stable periclinal chimeric albinism growth characteristic of the present invention.

Coast redwood trees (hereinafter "redwood") are well known in the industry for their disease and insect resistance, fast growth habit, fire tolerance, and for supporting wildlife habitat. Redwoods are also noted for their height and longevity. These characteristics have led to an increase of the use of this plant as an ornamental feature in landscaped gardens and re-forestation projects. Congruent with similar coast redwoods, the present invention is expected to reach a height of 18 to 36 meters, maintain tree form, and have a lifespan capacity of 200 to 1000 years.

Albinism in redwoods is a genetic mutation presenting chlorophyll deficiency in the plant's needles and stems. As chlorophyll is instrumental to glucose production and storage, albinism prevents a plant from providing food for itself; therefore, survival of albino growth is depended upon parasitic-type growth on the non-albino portions of the redwood. Albino redwoods (hereinafter "albino") in the wild are typically found in two forms: aerial and basal. Aerial albinos consist of a mutated branch where the foliage grows white or yellow. Basal albinos consist of entirely white or cream colored basal sprouts growing off an otherwise healthy green redwood. A chimeric redwood is a single plant organism with two or more different genotypes originating from the same bud or meristem. The normal green genotype acts as a surrogate to support the growth and survival of the albino mutation. It is not a symbiotic relationship between two separate plants. Further, due to this dependency and lack of chlorophyll, pure albino redwoods are unable to be reproduced vegetatively.

White color variation is subject to environmental conditions, particularly light exposure. For example, when grown in direct sunlight conditions, albino redwoods may turn ivory, cream, or light yellow in color. In contrast, when growing under the canopy of surrounding tree branches, albino redwoods are white in color. Excessive heat and low humidity may also result in die-back of the albino portions of the redwood. Additionally, the variation and distribution of white coloration is influenced by the phenotypic expression of three different types of chimeric growth: periclinal, sectorial, and mericlinal.

Chimerism in plants is typically achieved artificially through grafting and controlled gamma ray irradiation of seeds. One example of a grafted chimera plant is the thornless rose. A second example of irradiated seeds producing chimeric growth is the African violet plant. The present invention, in contrast, is a naturally-occurring chimeric mutation observed through variegated apical stems.

DEFINITIONS

In order to provide a clear and consistent understanding of the specification, the following definitions are provided:

A Zone. "A Zone" refers to a primary branch originating from a terminal bud. Coloration in the A Zone is predominantly green, but can range from range from albino, chimera, and non-chimeric variegation.

Albino. "Albino" refers to a white color variation ranging from ivory white to pale, yellow-green white, and is a result of a genetic mutation inhibiting chlorophyll production.

B Zone. "B Zone" refers to secondary branches developing from axillary and accessory buds from present or empty leaf axils with no primary branch present. They are commonly found between the internode of two primary branches. Coloration in the B Zone can range from albino, chimera, non-chimeric variegation, and less frequently green.

C Zone. "C Zone" refers to secondary branches developing from axillary and accessory buds in the region of the primary branch's axil or branch collar. Coloration in the C Zone can range from range from albino, chimera, non-chimeric variegation, and less frequently green.

Chimera. "Chimera" refers to the existence of more than one genotype present in one plant originating from the same bud or meristem. The chimeric phenotype is separated into three different categories based on the location and relative proportion of mutated to non-mutated cells in the apical meristem. These categories are mericlinal, periclinal, and sectorial.

Chimeric variegation. "Chimeric variegation" refers to a pronounced delineation of color with both green and white pigment in the meristems, branches, and needles.

Mericlinal chimera. "Mericlinal chimera" refers to a phenotypic expression in which only a small portion of the plant structure (stems, branches, and leaves) demonstrates chimeric albinism. This type of chimera is known in the industry to be unstable.

Non-chimeric variegation. "Non-chimeric variegation" refers to a partial lack of chlorophyll (and therefore green pigment) in plant cells and tissues where it is normally expected to be present. The pattern of variegation is unorganized and is differentiated at the cellular level between green and white. The variegation expression is mosaic in appearance.

Periclinal chimerism. "Periclinal chimerism" refers to a stable chimeric variegated mutation expressing albinism across the meristem dome. This leads to subsequent cell division of mutated and non-mutated cells within the meristem giving rise to a stable continuation of growth for both genotypes.

Primary. "Primary" as used in this application refers to branches and buds forming initially from the meristem with no rest period. Primary branches and buds develop within the "A Zone".

Secondary. "Secondary" as used in this application refers to branches and buds forming after a rest period and are latent in nature. They develop from axillary and accessory buds after Primary branch development. Secondary branches and buds are found both in "B and C Zones".

Sectorial chimera. "Sectorial chimera" refers to growth where mutated cells affect large sections of the apical meristem. Mutated tissue can extend through all cell layers within the meristematic tissue. The delineation line between both genotypes is usually vertical in arrangement through the meristem and between stomata bands in the leaves. This type of chimerism is known in the industry to be unstable.

BRIEF SUMMARY OF THE INVENTION

The following traits represent the characteristics of the new redwood tree variety 'Early Snow'. These traits in combination distinguish this variety from all other commercial varieties known to the inventors.

1. A non-grafted, periclinal chimera exhibiting stable albino growth from inside the apical meristem dome;
2. Terminal buds exhibiting phenotypic color expressions of green, albino, chimera or non-chimeric variegation with varying hues within these color expressions.
3. Latent, axillary and/or accessory buds forming between the internode of primary branches, branch axils, leaf axils, and within the branch collar zone, expressing a higher amount of albinism within the internode. These buds exhibit phenotypic color expressions of green, albino, chimera or non-chimeric variegation with varying hues within these color expressions. Frequently, axillary and/or accessory buds form in the absence of an existing branch, whether it's primary or secondary in nature.
4. Dark green short to medium length needles.
5. Branches with habit of horizontal to drooping-like habit with the shape of branchlets tapering towards a blunt end.
6. Moderate-to-fast growth depending on the amount of albinism.

The initial cross took place in 1976 under the direction of the second-named inventor, combined the premature cones on the green redwood (Parent Two) with pollen collected from the albino redwood (Parent One). The conelets were then sealed with a plastic bag to prevent open pollination. Redwood seeds take a year to mature, so in late 1977, of the thousands of seeds present, 360 were randomly selected from the ripe cones. Within a couple of weeks, several tiny stems and cotyledons emerged displaying differences in coloration. The present invention is derived from one of the 161 surviving seedlings of this experiment. Further background on the original cross are detailed in the book entitled *The White Redwoods: Ghosts of the Forest* (Davis, D. & Holderman, D. 1980, Naturegraph Publishers. California. Pages 33-36).

At the time of application filing, 'Early Snow' demonstrates a moderate-to-fast tree-like growth habit. It is approximately 1.86 m tall with a pointed top and a stem nearly 1.9 cm in diameter. The limb spread is approximately 96.5 cm in diameter. Sections exhibiting periclinal chimera and green foliage appear more dense then it's sibling 'Mosaic Delight' (U.S. Plant Pat. No. 26,573, hereinafter 'Mosaic Delight'). Forty percent of the present invention's branches exhibit periclinal chimeric growth with albino axillary bud growth. Propagated cuttings from the present invention already exhibit a faster growth rate than the original, first specimen. present invention A determination of growth rate for the cuttings is correlated with albinism. For example, when trees exhibit ratio of 0 to 25% albino foliage to green, they exhibit moderate to fast growth. With a ratio of 25 to 60% albino foliage to green, trees have a more moderate to slow growth rate. This expression reflects the impact of lower glucose levels in trees with high albinism and the effect on growth rate.

Past experimental propagation of 'Early Snow' underwent several propagation efforts and experienced several challenges in producing vigorous, stable specimens. Finally, the present invention has been successfully and repeatedly propagated asexually in a controlled nursery environment through vegetative, leaf and stem cuttings under the direction of the first named inventor. The first viable progation effort was conducted in the Fall of 2013 after the first-named inventor selected forty eight hardwood cuttings from the present invention. The cuttings were transported to a greenhouse located in Volcano, Calif. The cuttings were divided into stem cuttings, and dipped into a rooting solution consisting of 2500 PPM of IBA for approximately 10 seconds. Following this step, the stem cuttings were planted in gallon-sized pots and treated with a fungicide product. Between the Fall of 2013 through the Winter of 2013-2014, the cuttings were misted and given water at regular intervals. The cuttings were also provided supplemental lighting 24 hours a day. After 22 months in the propagation incubator 23 cuttings out of a total of 48 rooted. By the end of August of 2015 (second year), the cuttings demonstrated sharp increased albino growth from axillary and/or accessory buds forming within the internode and branch collar zone of the primary green branches.

The second propagation effort was conducted in the Winter of 2015 when the first-named inventor selected 14 hardwood cuttings. The cuttings were grown at the same greenhouse facility located in Volcano, Calif. and propagated under the same environmental conditions and protocol procedures carried out in Fall of 2013. By the Spring of 2016 (beginning the second year), the 7 surviving cuttings from both the 2013 and 2015 propagation groups demonstrated increased albino growth from axillary and/or accessory buds forming within the internode of primary green branches and within the branch collar zone of green branches. The results of the second propagation effort showed that they were consistent with the first.

Based on the results between the 2013 propagation group and the 2015 propagation group, the invention shows better rooting results with hardwood cutting propagation taken from summer growth rather than winter growth. During propagation experimentation, one cutting was selected for a fertilizer test and the conclusion of the test elucidates that a slow release fertilizer works best with 'Early Snow' and quick release fertilizers should be avoided. Tests have shown that cuttings from 'Early Snow' roots very easly in a favorable growing environment. Results have shown 48 to 50% of cuttings propagated rooted successfully with this invention.

The cuttings of 'Early Snow' have demonstrate that the combination of characteristics disclosed are stable and firmly fixed, and are retained true-to-type through the periclinal chimera genotypes. It is important to note that the invention can exhibit mericlinal and sectorial growth through the periclinal phenotype and therefore this growth is claimed within this invention. It is known in the literature that periclinal chimerism in plants is considered stable and as such, is readily available in commercial markets (Lineberger, R. No date. Origin, Development, and Propagation of Chimeras. Texas A&M University. Retrieved from http://aggie-horticulture.tamu.edu/tisscult/chimeras/chimeralec/chimeras.html on Jan. 20, 2014).

Table 1 illustrates variations in coloration and growth rate among six stem cuttings of the present invention.

TABLE 1

COLORATION AND GROWTH RATE COMPARISON

| Cutting | Type of Cutting | Height (cm) | New vertical growth (cm) | Axillary bud albinism (percentage) |
|---|---|---|---|---|
| #1 | stem | 186.7 | 171.7 | 40% |
| #2 | stem | 190.5 | 175.5 | 35% |
| #3 | stem | 219.7 | 204.7 | 20% |
| #4 | stem | 118.1 | 103.1 | 17% |
| #5 | stem | 63.5 | 48.5 | 50% |
| #6 | stem | 64.8 | 49.8 | 25% |

| Cutting | Tree canopy with terminal or lateral bud albinism (percentage) | Number of variegated secondary buds | Cutting propagated (year) | Age (measured on Sep. 8, 2016) |
|---|---|---|---|---|
| #1 | 5% | 51 | 2013 | 39 months |
| #2 | 7% | 84 | 2013 | 39 months |
| #3 | 7% | 36 | 2013 | 39 months |
| #4 | 1% | 37 | 2013 | 39 months |
| #5 | 5% | 28 | 2013 | 39 months |
| #6 | 0% | 25 | 2013 | 39 months |

Plant Breeder's Rights for this variety have not been applied for and 'Early Snow' has not been offered for sale more than a year before the filing date of this application, nor has it been offered for sale under another variety name. Since the original cross, cuttings of 'Early Snow' have undergone experimental use to solve prior propagation challenges and the present invention has not been publicly available during this time.

Plants of the present invention have not been observed under all possible environmental and cultural conditions. The phenotype may vary somewhat with variations in environmental conditions without, however, any variance in genotypes. For example, phenotypic expression may vary somewhat with fluctuations in temperature, light intensity and soil chemistry.

BRIEF DESCRIPTION OF THE PHOTOGRAPHS

The accompanying colored photographs illustrate the overall appearance of the new and distinct albino redwood tree with periclinal chimerism showing the colors as true as it is reasonably possible to obtain in colored reproductions of conventional photography. The photographs were taken in a greenhouse setting under defused, natural lighting. Two typical specimens (Stem Cutting Numbers 1 and 4) of the present invention are included to demonstrate color variation on the leaves and stems produced by the chimeric and non-chimeric genotypes.

FIG. 1 (taken Jan. 20, 2015 of Stem Cutting Number 1 at 31 months-old) is an overview of the tree exhbiting approximately 10% variegation towards the bottom of the plant. This illustrates the 1-year delay of the chimeric albino growth seen in this variety. Its typical with 'Early Snow' to have a majority of the green genotype emerge first in primary growth.

Figure 2:
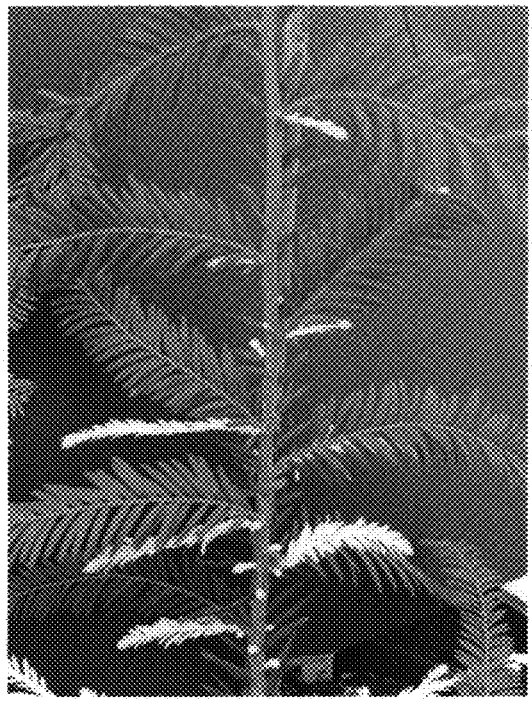

FIG. 2 (taken Jan. 20, 2015 of Stem Cutting Number 1 at 19 months-old) demonstrates the different areas of the plant where periclinal chimeric albinism is developing. Chlorophyll-deficient secondary, acessory, and axillary buds can be seen growing in the branch collar of primary branches with axillary buds forming in leaf axils on the stem.

Figure 3:
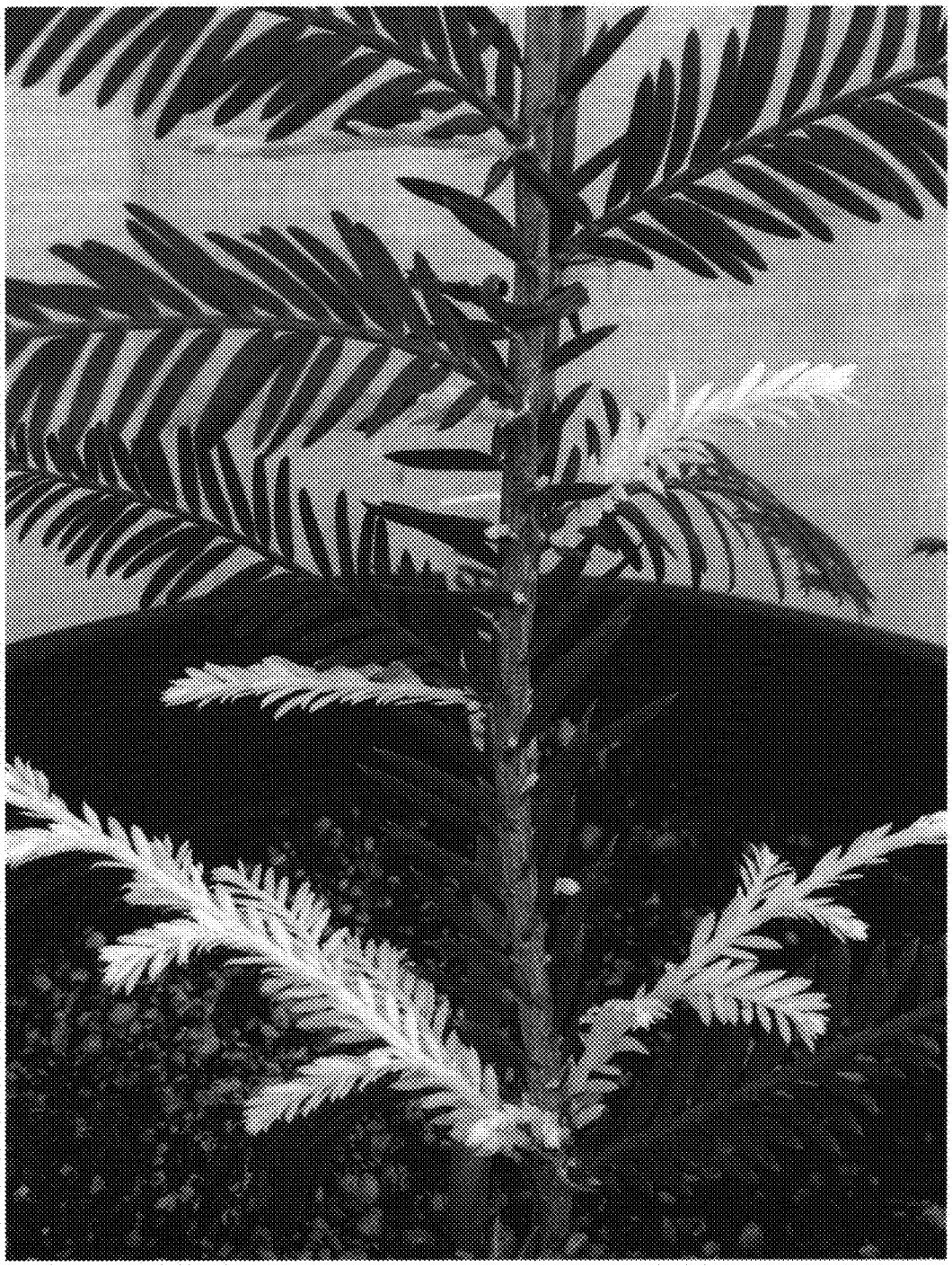

FIG. 3 (taken Oct. 6, 2014 of Stem Cutting Number 1 at 16 months-old) is a close-up image demonstrating the periclinal chimeric albinism originating from the apical meristem dome and displaying axillary and/or accessory buds forming within the internode of established green branches. These buds form in present leaf axils along the main stem between the internode of established primary green branches of the invention. There are also axillary and/or accessory buds exhibiting periclinal chimeric albinism in and around the branch collar zones of primary and secondary branches exhibiting green and white variegation.

Figure 3A:
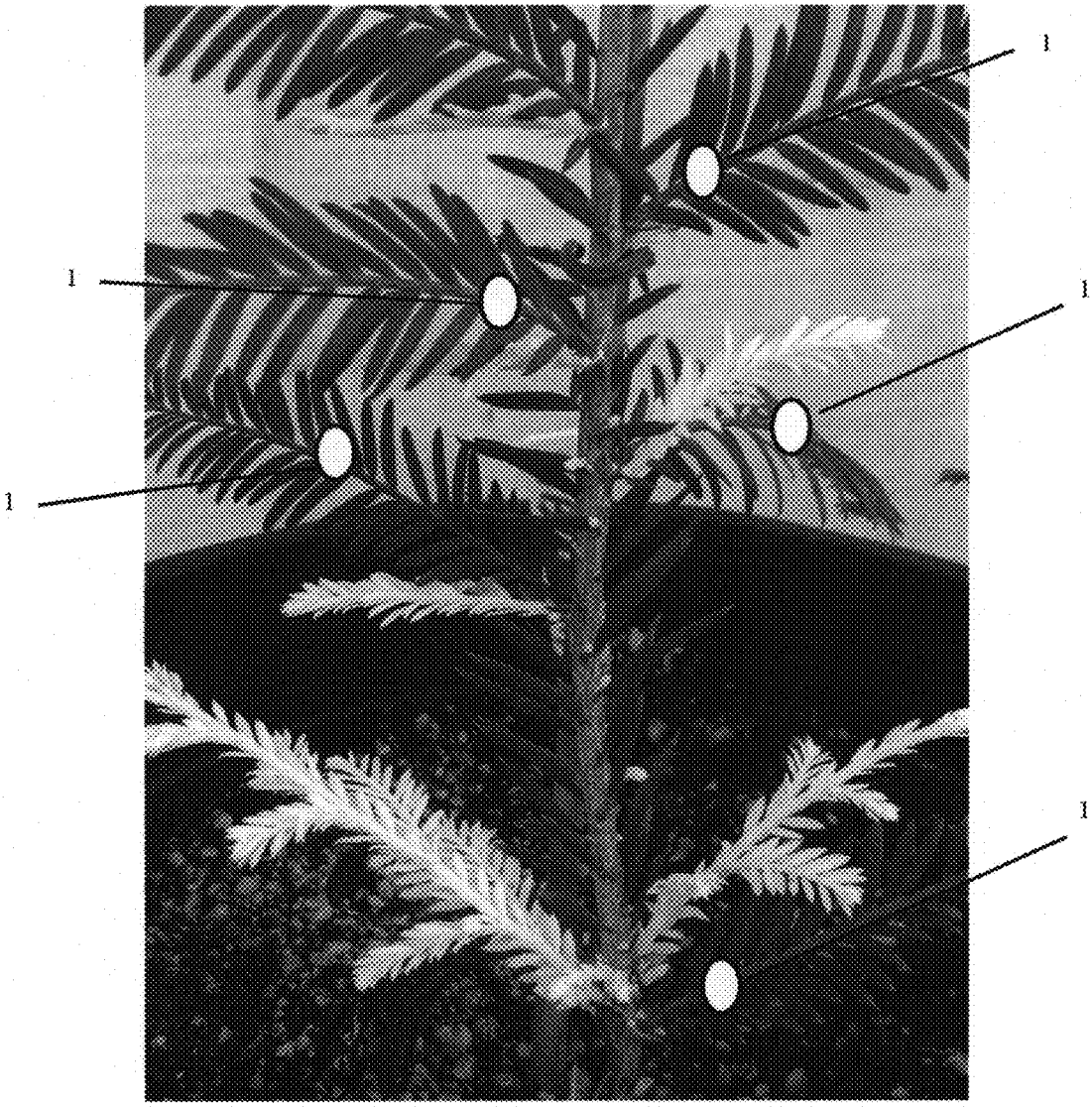

FIG. 3*a* (taken Oct. 6, 2014 of Stem Cutting Number 1 at 16 months-old) is similar to FIG. 3 except that Zones A are labeled with the number 1 to demonstrate the arrangement of the primary and secondary branches of all zones.

Figure 3B:
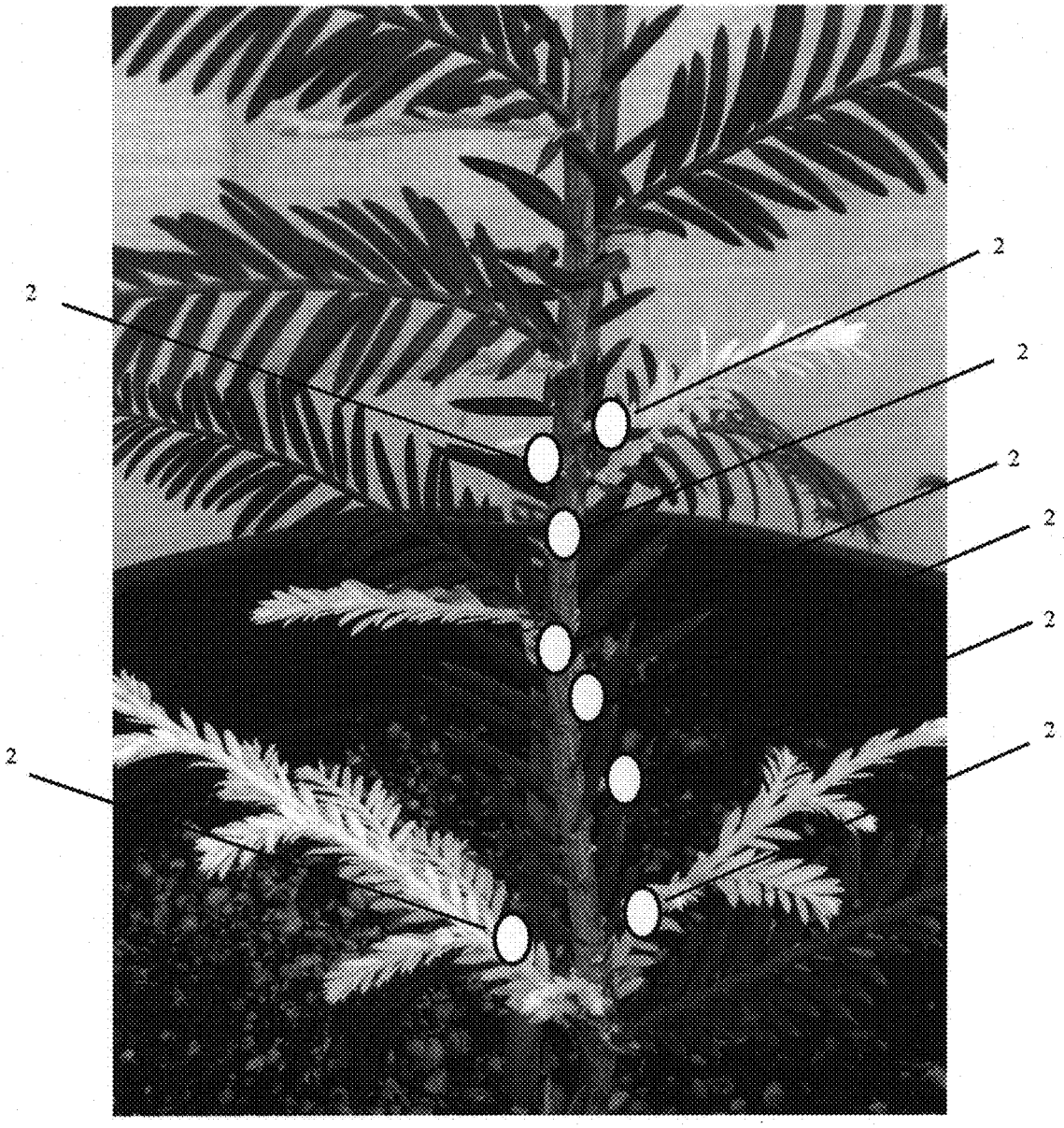

FIG. 3*b* (taken Oct. 6, 2014 of Stem Cutting Number 1 at 16 months-old) is similar to FIG. 3 except that Zones B are labeled with the number 2 to demonstrate the arrangement of the primary and secondary branches of all zones.

Figure 3C:
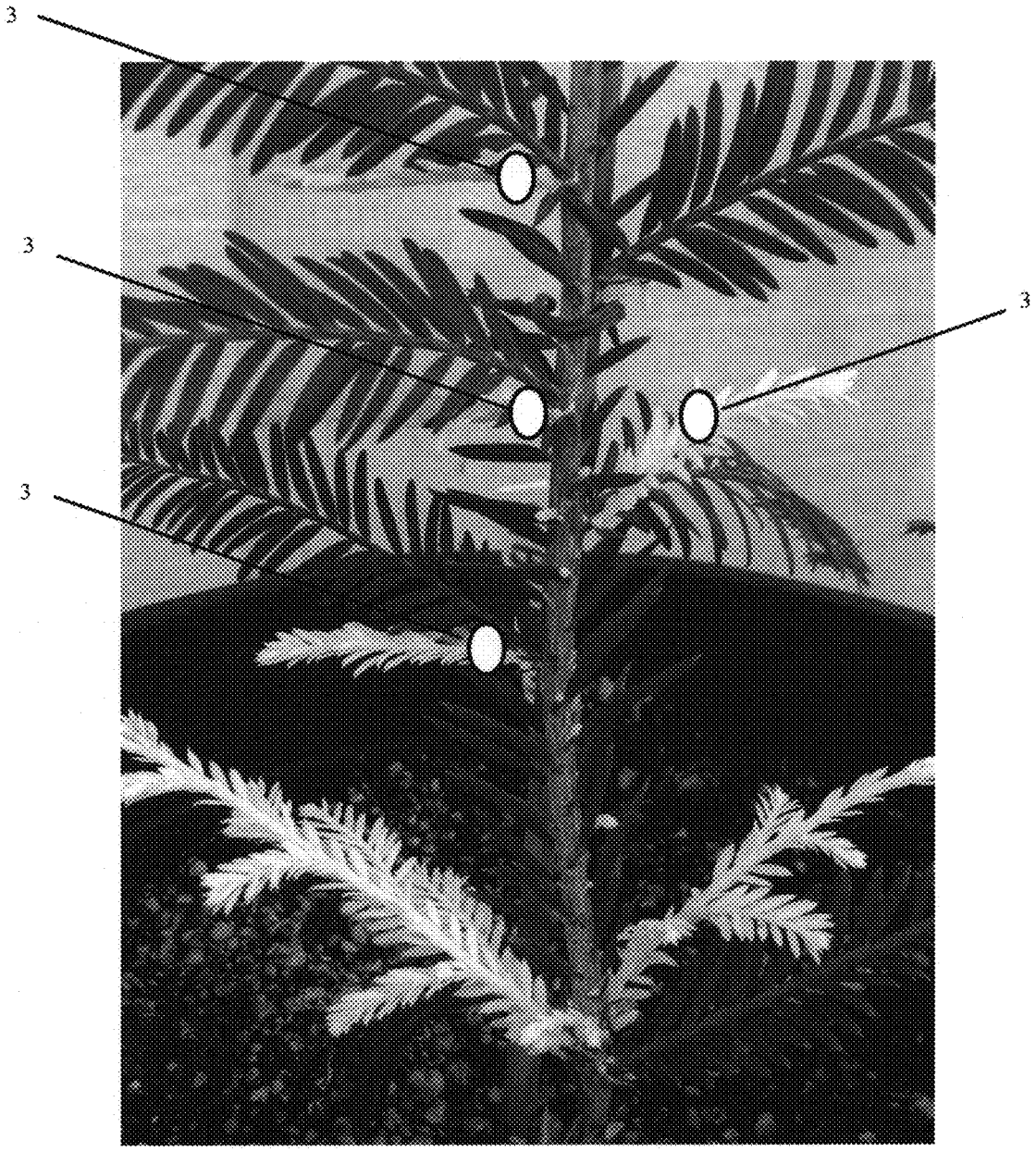

FIG. 3*c* (taken Oct. 6, 2014 of Stem Cutting Number 1 at 16 months-old) is similar to FIG. 3 except that Zones C are labeled with the number 3 to demonstrate the arrangement of the primary and secondary branches of all zones.

Figure 4:
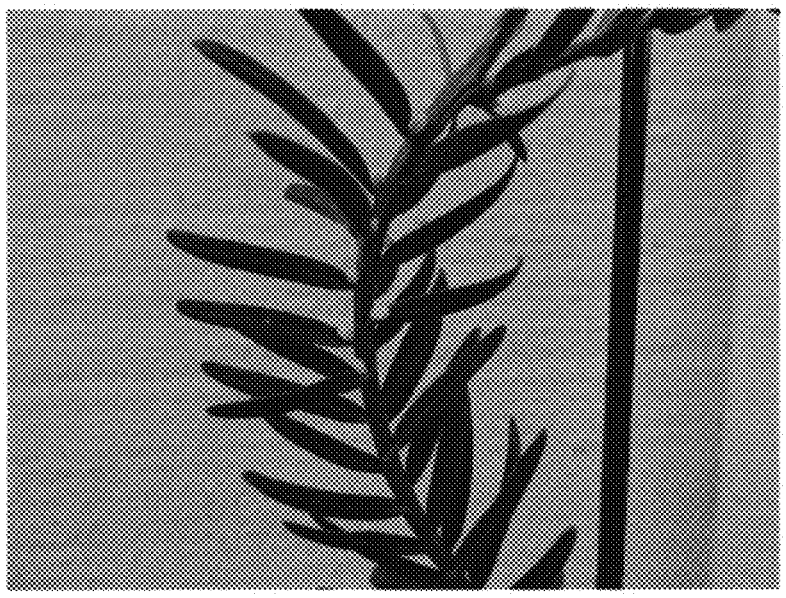

FIG. 4 (taken Oct. 17, 2015 of Stem Cutting Number 4 at 28 months-old) demonstrates a high proportion of chimeric albino expression found developing within needle axils between the internode of primary green branches. These type of buds are listed within the B Zone.

Figure 5:
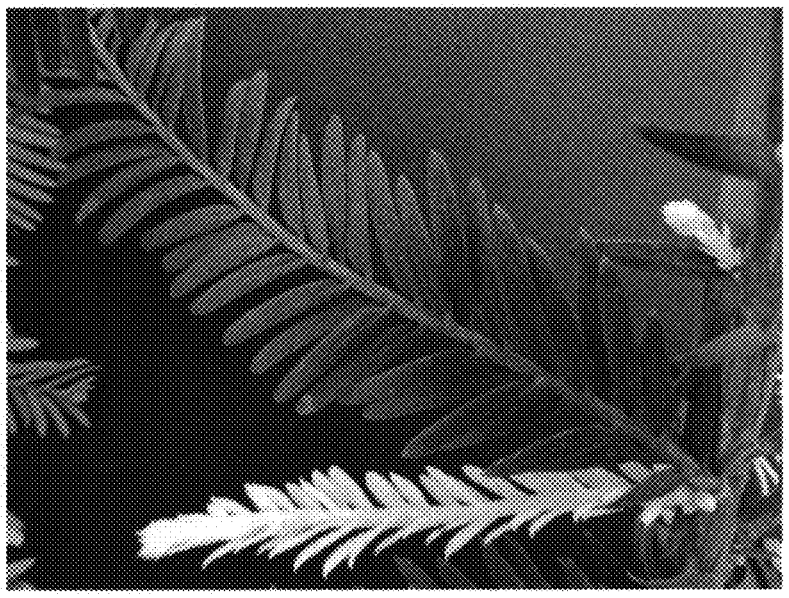

FIG. 5 (taken Jan. 20, 2015 of Stem Cutting Number 4 at 19 months-old) demonstrates chimeric albino expression on secondary branches arising from the branch collar's C Zone. Also exhibited are linear needles with obtuse, mucronate and acuminate tips commonly seen on this variety.

Figure 6:
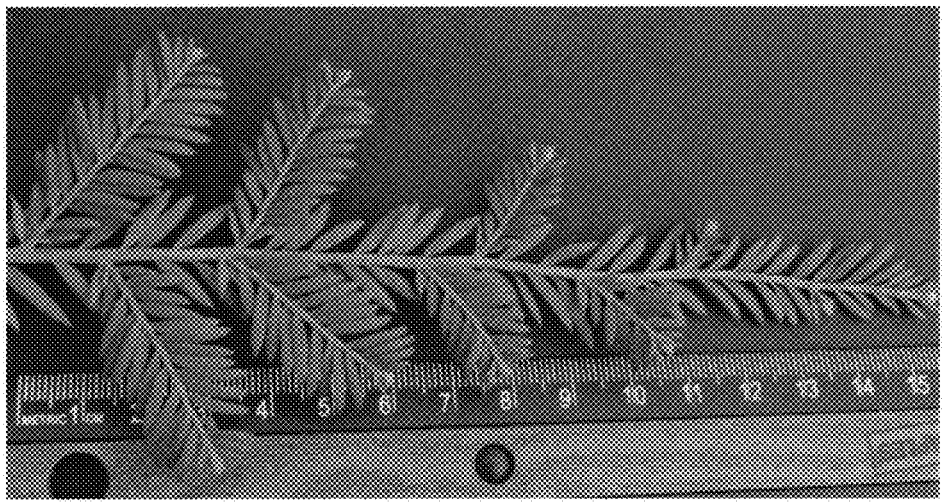

FIG. 6 (taken Jan. 11, 2015 of stem Cutting Number 1 at 19 months-old), exhibits sub-branchlets that taper to a point on primary branches. Needles on this variety tend to overlap on the branchlet leaving fewer gaps between needles compaired to sibings 'Mosaic Delight' and 'Grand Mosaic' (co-pending application, hereinafter 'Grand Mosaic').

Figure 7:
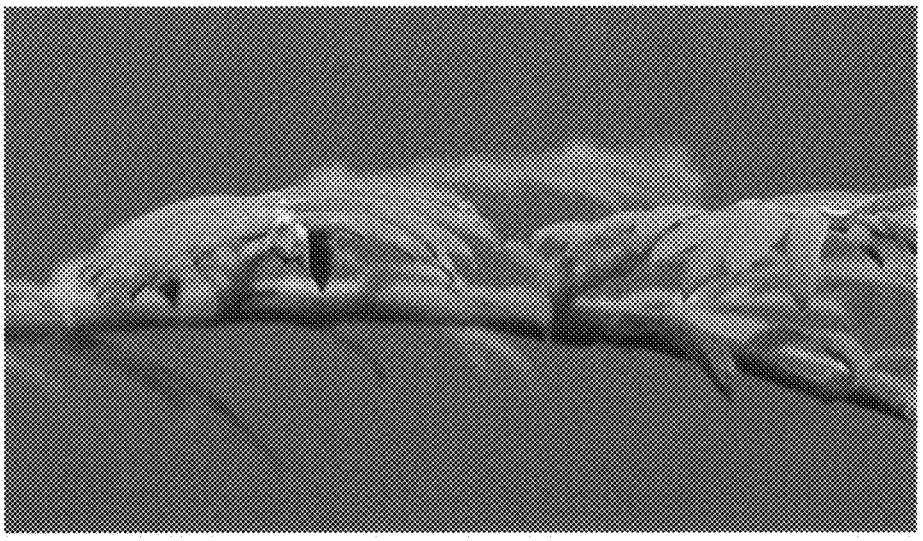

FIG. 7 (taken Jan. 11, 2015 of stem Cutting Number 1), shown with a direct view of the branchlet, exhibits a concave down needle pattern typically seen in this variety.

Figure 8:
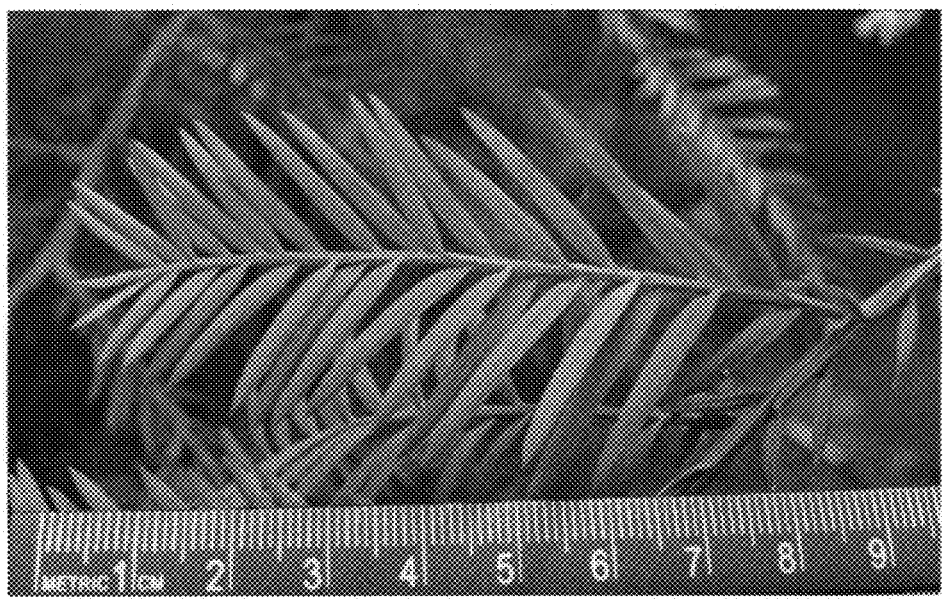

FIG. 8 (taken Jan. 11, 2015 of 'Grand Mosaic') presented as a compairson variety, demonstrates the broad needles and light green coloration of this variety. Needle tips exhibit acuminate points.

Figure 9:
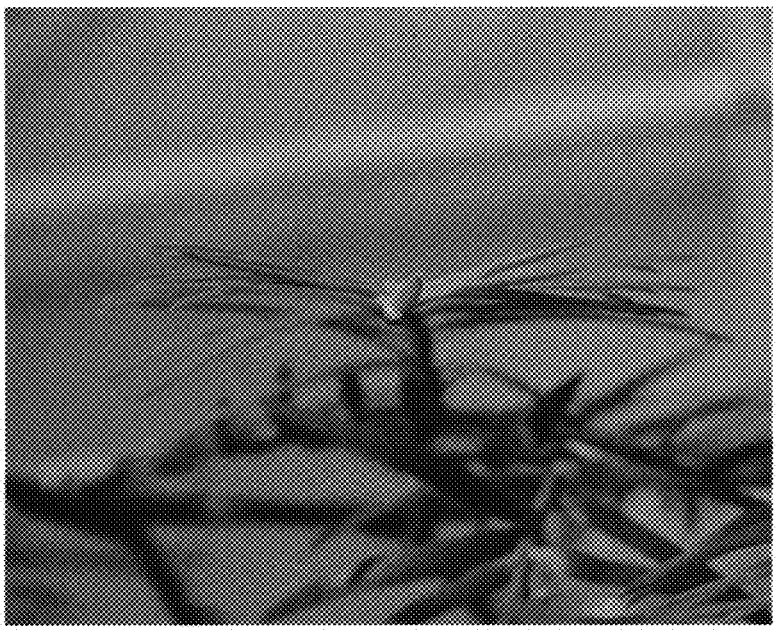

FIG. 9 (taken Jan. 11, 2015 of 'Grand Mosaic') presented as a compairson variety in direct view, exhibits a large horizontal needle pattern.

Figure 10:
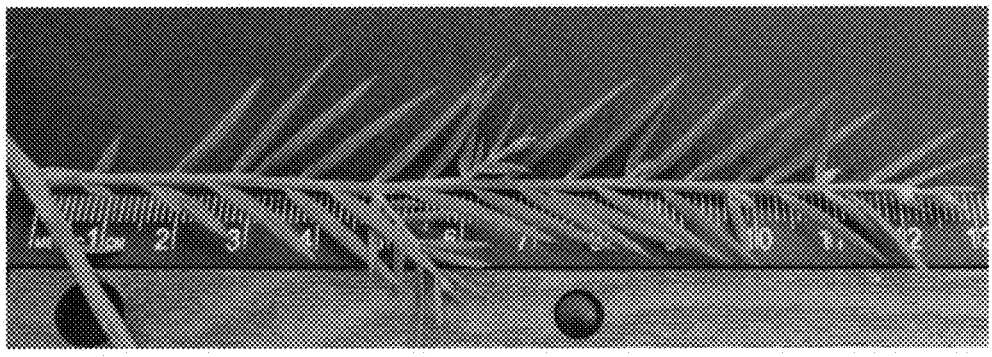

FIG. 10 (taken Jan. 11, 2015 of 'Mosaic Delight'), presented as a comparison variety, demonstrates an open needle arangment on the branchlets. Needles exibit a more narrow and wiry appearance compaired to 'Early Snow'.

Figure 11:
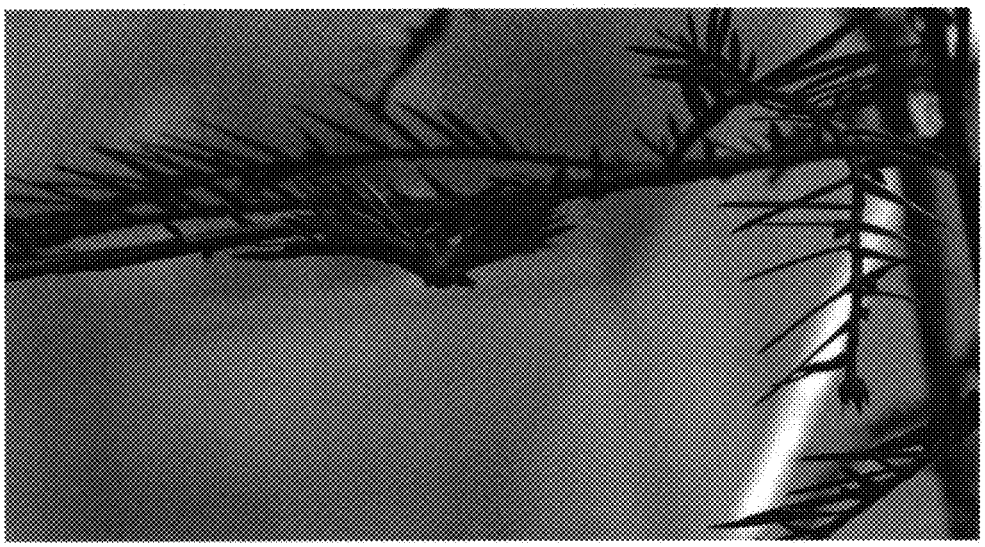

FIG. 11 (taken Jan. 11, 2015 of 'Mosaic Delight'), presented as a comparison variety, demonstrates an upturned "V" needle pattern on a direct view of the branchlet.

DETAILED BOTANICAL DESCRIPTION

The following is a detailed botanical description of the new variety 'Early Snow'. Data was collected from Stem Cutting Number 1 at 39 months-old in the Fall of 2016; presently growing in a greenhouse in Volcano, Calif. The growing conditions approximate those generally used in commercial practice. Color readings were observed indoors with natural lighting diffused through greenhouse panes. The color determinations are in accordance with the Fifth Edition (2007) of The Royal Horticultural Society Colour Chart published by The Royal Horticultural Society (London, England), except where general color terms of ordinary dictionary significance are used. Chimeric and non-chimeric expression among the propagated trees leads to a variation in color and, therefore, a color's hue, saturation, or intensity is generally depicted in The R.H.S. Colour charts through the follow color groups and ranges: RHS 4C-D, 8C-D (yellow group), 128A-149D (green group), and 155A-D, NN155-159D, 157A-158D, 189A-196D (grey group). Variegated color descriptions include both chimeric and non-chimeric expression.

TABLE 2

| VARIETY DESCRIPTION |
|---|
| Classification: |
| Family: Cupressaceae |
| Botanical: *Sequoia sempervirens* |
| Common: Coast Redwood tree |
| Parentage: |
| Parent One: Unnamed Albino *Sequoia sempervirens* (neither patented, nor commercially available) |
| Parent Two: Unconfirmed Green *Sequoia sempervirens* (however, it is believed that Parent Two is neither patented, nor commercially available) |
| Propagation: |
| Vegetative via leaf and stem cuttings |
| Plant: |
| Ploidy: Hexaploid |
| Height, unpruned (m): 186.7 cm (measured at 51 months); potential mature height of 18 to 40 m |
| Vigor: Strong |
| Shape: Pyramidal to pendulous |
| Growth rate: Moderate-to-fast depending on albinism present |
| Growth habit: Horizontal to pendulous |
| Canopy width (m): 96.5 cm |
| Canopy height (m): 186.7 cm |
| Crown shape: Pyramidal to pendulous |
| Trunk and Branchlets: |
| Trunk texture: Smooth as cuttings, emerging to fibrous at approximately four years |
| Trunk diameter (cm): 1.9 cm taken at 2.0 cm above the ground |
| Bark color (of a 2 to 3-year-old tree): RHS 165A and 200D; with a range of 164A-N167D, 173A-178D, and 200A-D |

TABLE 2-continued

VARIETY DESCRIPTION

Branchlet length (m): 58.4 cm measured from stem
Branchlet texture: Smooth and waxy
Branchlet color: Variation due to chimeric expression, including: green, white, chimeric, or non-chimeric variegated
New growth, green branchlet: RHS 144A (green group), with a range of 146B-D (green group)
Old growth, green branchlet: RHS N137A, (green group), with a range of RHS N137A-D, 137A-D and 147A-B (green group)
New growth, albino branchlet: RHS 155A (gray group) with a range of 155A-D, NN155A-B, 158C-D (grey group)
Old growth albino branchlet: RHS 4D and 8D, (yellow group), with a range of 4C and 8C (yellow group), and a range of 158C-D (grey group)
Variegated branchlet: Ranging from RHS 4D and 8D (yellow group) to RHS 128A-149D (green group) to RHS 155A-D, NN155-159D, 157A-158D, and 189A-196D (grey group)
Branchlet arrangement: Alternate
Crotch angle from main trunk:
Green branches: Horizontal range from 0° to 20° and dropping range from 100 to 3000
Albino, chimeric, or non-chimeric variegated branches: Approximately 300° to 45°
Meristematic bud:
a. Shape: Scaly
b. Color:
Apical meristem: Chimeric
Lateral buds, axillary and/or accessory buds forming in and around the branch collar zone exhibiting phenotypic color expressions ranging from green, albino, chimera or non-chimeric variegation
Green bud: RHS 144A, with a range of RHS 143A-D, 144A-D, 146B-D (green group)
White bud: 155A (grey group) with a range of 155A-D, NN155A-B, 158C-D (grey group)
Variegated bud: Ranging from RHS 4D and 8D (yellow group) to RHS 128A-149D (green group) to RHS 155A-D, NN155-159D, 157A-158D, and 189A-196D (grey group)
c. Bud-union characteristics: Axillary and accessory
Burl: Non observed
Scion:
Circumference (leaf cuttings): 3.5 cm
Height at which measurement taken: 15.2 cm at time of planting and 186.7 cm for stem cuttings
Suckering: None observed
Leaves:
Arrangement: Flat to concave needles in alternating patterns
Texture: Glabrous (smooth)
Type: Simple
Shape: Needle-like
Needle tip shape: Acuminate, obtuse, mucronate
Cross section: Concave 1.0 mm
Leaf needle length (mm): 1.0 to 3.5 cm
Leaf needle width (mm): 0.5 to 1.0 cm
Surface:
a. Upper surface texture: Glabrous (smooth, waxy)
b. Surface color (upper and lower): Green, white, chimeric, or non-chimeric variegated-specifically:
New growth, green needle (upper surface): RHS 144A with a range of 146B-D (green group)
New growth, green needle (lower surface): RHS 194C (grey group), with a range of 192A-D, 193A-C, 194D (grey group)
Old growth, green needle (upper surface): RHS N137A (green group), with a range of N137A-D, 137A-D and 147A-B (green group)
Old growth, green needle (lower surface): RHS 191B (grey
group), with a range of 190A-C, 191A-D (grey group)
New growth, albino needle (upper surface): RHS 155A (grey group) with a range of 155A-D, NN155A-B, 158C-D (grey group)
New growth, albino needle (lower surface): RHS NN155A (grey group), with a range of NN155A-B, 155A-D, and 158C-D (grey group)
Old growth, albino needle (upper surface): RHS 4D and 8D (yellow group)
Old growth, albino needle (lower surface): RHS 4D and 8D (yellow group), with a range of 4C and 8C (yellow group) and 158A-D, (grey group)
Variegated needles in all locations: Ranging from RHS 4D and 8D (yellow group) to RHS 128A-149D (green group) to RHS 155A-D, NN155-159D, 157A-158D, and 189A-196D (grey group)
c. Stomata band(s) on lower needle: Present, 2 bands
Petiole:
a. Shape: Oval and scale-like
b. Color: Green, white, chimeric, or non-chimeric variegated, specifically:
New growth, green petiole: RHS 144A with a range of 146B-D (green group)
Old growth, green petiole: RHS 137A (green group), with a range of N137A-D, 137A-D, and 147A-B (green group)
New growth, albino petiole: RHS 155A (grey group) with a range of 155A-D, NN155A-B, 158C-D (grey group)
Old growth, albino petiole: RHS 4D and 8D (yellow group)
Variegated petiole: Ranging from RHS 4D and 8D (yellow group) to RHS 128A-149D (green group) to RHS 155A-D, NN155-159D, 157A-158D, and 189A-196D (grey group)
c. Thorns (spines): Absent
d. Length (average): 2.5 cm to 3.0 cm (leaf lamina narrows down proximally)
Cones: None observed
Flowers: None observed
Reproductive Organs: None observed
Best mode growing conditions:
Soil conditions: Deep, well-drained loam and clay-loam soil
Water use/drought tolerance: Require regular watering when young; however, once established, trees are mildly drought tolerant with optimal growing conditions including an annual rainfall exceeding 102 cm per year
Temperature: Best grown in cool climates ranging from 50° F. to 80° F. with frost-free winters
Fertilization:
a. Propagation: Potting soil with slow release fertilizer
Maintenance: Slow release fertilizer
Resistance to disease: Low susceptibility to disease due to tannin content; however, may be subject to *Botryosphaeria* sp. canker if under stress conditions (for example, drought).

COMPARISON TO SIMILAR VARIETIES

Parent One is a non-chimeric variegated albino *Sequoia sempervirens* demonstrating ninety-five percent albinism with approximately five percent non-chimeric variegation on the new growth and a hedge-bush-like growth habit. 'Early Snow' displays an apically weak tree form with both chimeric
and non-chimeric variegated growth. Specifically, 'Early Snow' demonstrates stable green and chimeric albino growth from inside the apical meristem with albino to mosaic variegation displayed on terminal, lateral, adventitious, axillary, and accessory buds. These buds form between the internode of established green branches, inside present or empty branch axils and within the branch collar zone. 'Early Snow' also demonstrates horizontal to weeping-like chimeric branches that are either green, albino, or chimeric (periclinal, mericlinal, or sectorial).

The exact parentage of Parent Two is unconfirmed; however, during the 1976 cross, Parent One was crossed with several nearby standard green *Sequoia sempervirens* exhibiting characteristics typical of redwoods grown locally in Santa Cruz, California. Unfortunately, precise records of the crosses do not elucidate which of the potential green *Sequoia sempervirens* is the female parent of this invention. Typical of the trees in this location, Parent Two is an old growth, and slow-growing tree without any variegation or chimeric albino growth. In contrast, 'Early Snow' grows at a moderate-to-fast rate, and displays a range of coloration through the chimeric and non-chimeric variegated growth.

The commercially available *Sequoia sempervirens* named 'Aptos blue' demonstrates blue-green foliage and an upright habit with small weeping side branches; whereas, 'Early Snow' foliage ranges in color from green, albino, chimeric, and non-chimeric variegated and has horizontal to drooping branches.

TABLE 2-continued

| VARIETY DESCRIPTION |
|---|
| Sibling variety 'Mosaic Delight' exhibits similar chimeric albino expressions to 'Early Snow' with notable differences. Needles on 'Early Snow' are darker green and dense in appearance compared to 'Mosaic Delight', which has narrow and medium green coloration. Needle tips on 'Early Snow' exhibit multiple shapes: obtuse, mucronate and acuminate. In comparison, 'Mosiac Delight' generally exhibits acuminate tips. 'Early Snow' exhibits higher chimeric albino growth within the internode region of established green branches than in 'Mosaic Delight', which primarily expresses chimeric albino growth from the branch collar zone of established branches. Overall 'Early Snow' exhibits a higher rate of white áxillary and accessory buds develping within leaf axils compared to 'Mosaic Delight'. Further,'Early Snow' differs from 'Mosaic Delight' in that its growth rate is strong, whereas, 'Mosaic Delight' is weak; the albino growth in the internode in 'Early Snow' is higher than in 'Mosaic Delight' and the needle arrangement is overlapping and concave, whereas, in 'Mosaic Delight' it is upturned and open. Additionally, 'Early Snow' exhibits weak apical dominance compared to 'Grand Mosaic' which is mostly apically strong instature. Although 'Early Snow' can maintain a tree form when trained, the natural tendency of the variety is to remain in bush like form. Lastly, 'Early Snow' is particularly distinguished by its short to medium length needles with an overlapping and concave arrangement, a combination of dark green needles exhibiting both sharp and blunt rounded tips. In comparison, 'Mosaic Delight' exhibits an open needle arrangment with medium length needles with a sharp needle tips. Sibling variety 'Grand Mosaic' exhibits similar chimeric albino expressions to 'Early Snow' with notable differences. Axillary and accessory buds forming in the 'B' zone (between primary branches) on 'Grand Mosaic' predominately form from empty leaf axil whereas with 'Early Snow', a needle is usually present. Overall 'Early Snow' exhibits a higher rate of white axillary and accessoroy buds develping within leaf axils compared to 'Grand Mosaic'. Further, 'Early Snow' differs from its patent pending sibling 'Grand Mosaic' in that its apical dominance is weak, whereas 'Grand Mosaic' exhibits strong apical dominance; 'Early Snow' tends to exhibit albino expression with a 1-year delay, whereas, 'Grand Mosaic' tends to exhibit albino expression with a 2 to 4-year delay. 'Early Snow' also has short to medium size needles and 'Grand Mosaic' has long needles. Lastly, the green needles of 'Early Snow' are dark in comparison to those of 'Grand Mosaic', which are light green. |

Table 3 highlights the distinctions between 'Early Snow' and its siblings. One clone from each of the siblings propagated in 2013 was measured for total height. Then all "B Zone" and "C Zone" secondary branches were counted on each siblings' main axis. After the count, a ratio of B to C Zone was established to determine the percentages of each. Since each invention's height varies, the total of each B and C Zones was divided into the height of the tree to determine the average height (centimeters) for B and C Zone branches respectively. The data tabulated below illustrates the different growing patterns discovered within B and C Zone secondary branches and was collected the Winter of 2015.

TABLE 3

COMPARISON OF SECONDARY BRANCHES PATTERNS AMONG SIBLINGS

| Date Jun. 2, 2015 | Height (cm) | Age | Number of B & C | Percentage of B & C | B & C per cm on main axis | Secondary development after primary |
|---|---|---|---|---|---|---|
| 'Mosaic Delight' | 159.4 | 4 years | B = 10<br>C = 35 | B = 22%<br>C = 78% | B = 15.9 cm<br>C = 4.6 cm | 1-2 years |
| 'Grand Mosaic' | 221.6 | 4 years | B = 27<br>C = 14 | B = 66%<br>C = 34% | B = 8.2 cm<br>C = 15.8 cm | 2-4 years |
| 'Early Snow' | 97.2 | 2 years | B = 20<br>C = 19 | B = 51%<br>C = 49% | B = 4.9 cm<br>C = 5.1 cm | 1-2 years |

Findings in Table #3 demonstrate that 'Early Snow' produces nearly equal amounts of buds from B and C zones. This balanced distribution of variegated buds is thought to enhance 'Early Snow's visual appearance and marketablity when compaired to siblings: 'Mosaic Delight' and 'Grand Mosaic'.

Table 4 presents a side by side comparison of the sibling varieties from the original cross experiments conducted in 1976. The siblings were grown in the same environmental conditions and exhibit the following similarities and differences.

TABLE 4

COMPREHENSIVE GROWTH PATTERNS COMPARISON AMONG SIBLINGS

| Characteristic | 'Mosaic Delight' Sibling PP | 'Grand Mosaic' Sibling Present application | 'Early Snow' PPAF |
|---|---|---|---|
| Growth rate | Weak | Strong | Strong |
| Apical dominance | Weak | Strong | Weak |
| Albino expression | 1-year delay | 2 to 4-year delay | 1-year delay |
| Albino growth in internode | Lower | Higher | Higher |
| Majority of "B" zone buds found | Leaf axils | Empty leaf axils | Leaf axils |
| Needle angle | "V" shaped | Horizontal | Concave down |
| Needle density | Open | Dense | Dense & overlapping |
| Needle length | Medium | Long | Short to medium |
| Needle shape: linear | Linear with Acuminate tip | Linear with Acuminate tip | Linear with Obtuse, mucronate and acuminate tips |
| Needle color | Dark green | Light Green | Dark green |
| Branchlet shape | Narrow towards blunt end | Wide towards a blunt end | Tapers towards a blunt end |

We claim:

1. A new and distinct variety of albino chimeric redwood tree, as illustrated and described herein.

* * * * *